United States Patent [19]
Bernard et al.

[11] 4,416,806
[45] Nov. 22, 1983

[54] CATALYST FOR PRODUCTION OF AROMATIC HYDROCARBONS AND PROCESS FOR PREPARATION

[75] Inventors: Jean-René Bernard, Serezin du Rhone; Michele Breysse, Villeurbanne, both of France

[73] Assignee: Elf France, Paris, France

[21] Appl. No.: 471,902

[22] Filed: Mar. 4, 1983

Related U.S. Application Data

[63] Continuation of Ser. No. 272,176, Jun. 10, 1981, abandoned.

[51] Int. Cl.$^3$ .............................................. B01J 29/12
[52] U.S. Cl. ...................................... 502/74; 585/419; 502/77; 502/79
[58] Field of Search .................... 252/455 Z; 585/411, 585/419; 208/138

[56] References Cited

U.S. PATENT DOCUMENTS

| | | | |
|---|---|---|---|
| 3,415,737 | 12/1968 | Kluksdahl | 208/138 X |
| 3,775,502 | 11/1973 | Oishi | 208/138 X |
| 3,819,507 | 6/1974 | Oishi | 208/139 |
| 4,048,058 | 9/1977 | Petersen et al. | 208/138 |
| 4,104,320 | 8/1978 | Bernard et al. | 208/138 X |
| 4,210,524 | 7/1980 | Antos | 585/419 X |
| 4,246,095 | 1/1981 | Antos | 208/138 X |

FOREIGN PATENT DOCUMENTS 2360540  3/1978  France .................. 585/419

Primary Examiner—Carl F. Dees
Attorney, Agent, or Firm—Burgess, Ryan & Wayne

[57] ABSTRACT

Monofunctional dehydrocyclization catalyst of paraffins, characterized in that it contains: 0.1 to 1.5% platinum, o.1 to 1.5% rhenium incorporated in the form of carbonyl, a small proportion of sulphur introduced by a sulphur compound reducible or decomposable by hydrogen such that the ratio x of the number of sulphur atoms to the number of platinum and rhenium atoms deposited on the catalyst be comprised between 0.05 and 0.6, the carrier being constituted by a zeolitic crystalline aluminosilicate compensated in more than 90% by alkaline cations having a pore diameter of more than 6.5 Angstroms.

32 Claims, No Drawings

CATALYST FOR PRODUCTION OF AROMATIC HYDROCARBONS AND PROCESS FOR PREPARATION

This application is a continuation, of application Ser. No. 272,176, filed June 10, 1981 abandoned.

The invention is directed to a novel catalyst for dehydrocyclization of paraffins having from 6 to about 10 carbon atoms and with the method of preparation thereof. This catalyst is especially effective for the production of light aromatics from petroleum fractions obtained by direct distillation.

The customary methods for carrying out aromatization reactions are based on the use of catalysts comprising a noble metal on a carrier, especially catalysts containing from 0.2 to 0.8% by weight platinum on an alumina carrier chlorinated to 0.5-2% by weight. It is generally believed that these catalysts work by a bifunctional mechanism that combines the hydrogenating dehydrogenating activity of the metal and the isomerizing cyclizing activity of the acid carrier. A very important improvement in these catalysts was the addition of a second metal to the catalyst, which provided increased stability and activity to permit operation at a lower pressure under conditions where the aromatization reactions are favored.

U.S. Pat. No. 3,415,737 (H. E. KLUKSDAHL, Chevron Res. Co.) shows the advantage of using catalysts containing from 0.1 to 3% Pt and from 0.1 to 3% rhenium. It also claims the presence of 0.05 to 2% sulphur on the catalyst, said sulphur being meant to limit the hydrogenolyzing activity due to the rhenium, which activity leads to a quick deactivation of the dehydrocyclization catalyst.

Another type of aromatization catalyst is described in U.S. Pat. Nos. 3,775,502 and 3,819,507 (M. IOSHI Sun Res. and Dev. Co.). It consists of platinum deposited on zeolites X exchanged with lithium, sodium or potassium. This catalyst can also contain from 0.1 to 1.2% by weight rhenium. The aromatizing activity of this type of catalyst is comparable to that of the preceding catalysts. The presence of rhenium in this new type of catalyst does not seem to provide any advantage, since the results obtained using the platinum-rhenium zeolite X catalyst are inferior to the results obtained using the Pt on the zeolite X catalyst.

Another type of catalyst on a molecular sieve is described in U.S. Pat. No. 4,104,320 (J. Nury, J. R. Bernard, ERAP). It contains from 0.1 to 1.5% by weight platinum deposited on alkaline zeolite L preferably exchanged with potassium, rubidium or cesium. When charged with platinum, zeolite L provides a yield and selectivity superior in aromatics to all the other catalysts described above. Even though the working mechanism of these catalysts has not been entirely elucidated, it is believed that this catalysis is monofunctional and that its activity is due solely to the platinum, the properties of the platinum being modified by the zeolite L carrier. The zeolite L used for said catalysts is exchanged with alkaline cations and for that reason the platinum that is in a metallic state under the conditions of the catalysis is strongly influenced by the alkaline cations. The activity of the catalyst increases when one goes from lithium to potassium and to cesium.

However, although they possess remarkable selectivity and aromatizing activiy, the catalysts described in the patent cited have a low stability which is inferior to the stability of the monometallic bifunctional catalysts having a base of platinum on chlorinated alumina and for this reason, they can only be used under high hydrogen pressures if it is desired to obtain long cycle times.

In trying to stabilize said catalysts, it is possible to use the techniques described in the preceding patents, namely, the incorporation of rhenium into the catalyst by contacting the catalyst with perrhenic acid in an aqueous solution. This incorporation, whether effected by coimpregnation with the platinum or by successsive impregnation, does not lead to an improvement on the catalytic stability and in addition, the activity of the bimetallic catalysts is clearly inferior to the activity of the monometallic catalysts supported on zeolite L. This is in agreement with the observations of the inventors of U.S. Pat. No. 3,819,507 who did not notice any beneficial effect from the addition of rhenium to the platinum-charged zeolites X and Y.

We have unexpectedly discovered that the incorporation of rhenium in the form of rhenium carbonyl $Re_2(CO)_{10}$ into a zeolite preceded or followed by the deposition of platinum by the known methods (impregnation, ionic exchange of salts or complexes of platinum) provides dehydrocyclization catalysts with good catalytic activity and stability after reduction by hydrogen.

British Pat. No. 2,004,764 describes a catalyst prepared by pyrolysis of rhenium carbonyl on a porous carrier containing platinum. This patent shows that the catalysts thus prepared are more active than the catalysts prepared by means of perrhenic acid, since they permit the obtention, in reforming, of products having a higher octane index at the same reaction temperature. However, these catalysts produce more hydrocracking than the catalysts prepared from perrhenic acid, and therefore they do not provide a real advantage.

On the other hand the use of rhenium carbonyl in the Pt-Re-zeolite catalysts makes it possible to obtain an active catalyst while the use of perrhenic acid leads to a catalyst with poor activity.

However, with these catalysts, the selectivity for the dehydrocyclization of paraffins is poor. These catalysts produce a hydrogenolysis in similar proportions to the bifuntional catalysts on a chlorinated alumina carrier. The catalyst obtained is easily poisoned and is practically not active in dehydrocyclization.

We have unexpectedly discovered that the incorporation of sulphur in the catalyst, in proportions much smaller than those previously described, leads to good selectivities with excellent catalytic stability. For example, the sulphur content ordinarily recommended for ready-to-use reforming catalysts is in the range of 0.2% by weight deposited by impregnation with a sulphurated compound or presulphuration prior to catalysis, which corresponds to a molar ratio x of about 2 for contents of 0.3% Pt and 0.3% Re. X designates the ratio of the number of sulphur atoms deposited on the catalyst to the number of Pt+Re atoms contained in the catalyst.

When the value of the molar ratio of sulfur to metal in the platinum-rhenium-zeolite catalysts is in the range of about 2, the catalysts are not active. It is necessary to reduce the molar ratio x to between about 0.5 and 0.6 to obtain a catalyst that is active and stable for dehydrocyclization. For the Pt and Re contents mentioned above, this corresponds to about 0.005% to 0.06% by weight of sulphur on the catalyst, which is remarkably less than the 0.2% by weight mentioned above.

BRIEF DESCRIPTION OF THE INVENTION

The invention is a new catalyst for dehydrocyclization of paraffins containing from 0.1 to 1.5% platinum, from 0.1 to 1.5% rhenium, sulphur in a form reducible or decomposable by hydrogen such that the molar ratio x of sulphur atoms to Pt and Re atoms is between about 0.05 and 0.6, the carrier comprising a zeolitic crystalline aluminosilicate of a pore size larger than 6.5 Angstroms exchanged more than 90% by alkali metal cations.

The invention also comprises a novel process for preparations of a catalyst comprising the following steps, taken in any order:

(a) charging a non-acid zeolitic crystalline aluminosilicate carrier having a pore size larger than 6.5 Angstroms with rhenium, said charging being effected by means such as sublimation of rhenium carbonyl $Re_2(CO)_{10}$ on the carrier or by impregnating the carrier with an organic solution of $Re_2(CO)_{10}$, (b) depositing platinum on the carrier by methods known in the art, such as impregnation by a solution of a platinum compound such as hexachloroplatinic acid, tetraamine platinum chloride, dinitro diamino platinum, or ion exchange with a cationic complex of platinum.

(c) introducing sulphur into the carrier by means such as a solution of a sulphurated compound that can be reduced or decomposed under the conditions of the catalysis (oxyanion, sulphur, mercaptan, etc.), it being possible to carry out this operation at the same time as the preceding one. It is also possible to pretreat the catalyst in the dehydrocyclization reactor by contacting the catalyst with a sulphurated compound ($H_2S$, dimethyl disulphide, $CS_2$) before or after reduction by the hydrogen.

After carrying out these steps, the catalyst is dried, calcined, reduced with hydrogen and can be sulphurated if desired, as described above.

The catalysts of the invention possess exceptional aromatizing properties and excellent stability.

DETAILED DESCRIPTION OF THE INVENTION

The carrier comprises a zeolitic crystalline aluminosilicate or molecular sieve. It is essential for the dehydrocyclization that the molecular sieve serving as a carrier have only a slight acidity, no acidity or a slight basicity. The zeolite must have its cationic sites of exchange exchanged with more than 90% of alkaline cations. The other cations introduce a certain acidity either because they are multivalent and thus create acid sites or because they can be reduced or decomposed under the conditions of the catalysis, the reduction or decomposition corresponding to the formation of protons on the zeolite.

It is evident that the pores of the alkaline zeolite must have a size at least equal to the dimensions of the benzene molecule. The zeolites which are useful are the faujasites X and Y, zeolite L, zeolite omega and zeolite ZSM 4. These zeolites can be used in their form as synthesized, except for zeolite omega and ZSM 4 which contain alkylammonium cations which must be replaced by alkali metal cations by the methods known to those skilled in the art such as thermal decomposition followed by neutralization by an alkali metal basic material. It is also possible to exchange the snythesis cations by other alkali metal cations and the zeolites in question can therefore contain lithium, sodium, potassium, rubidium and/or ceesium.

Among the zeolites, the preferred carrier is zeolite L which provides exceptional yields of aromatics from aliphatic fractions. Zeolite L is synthesized in its potassium form and can be economically used as such, but it can also contain sodium and especially rubidium or cesium.

The zeolitic carrier is generally shaped before it is used industrially. The shaping can be effected before or after the depositing of the platinum, rhenium and sulphur by methods known to those skilled in the art such as by use of alumina or clay binders and extrusion or molding in the form of small balls by the technique of the dragee maker or of the oil drop. Another technique that can be used is shaping in the form of small balls or extrusion of a clay such as metakaolin and conversion thereof to zeolite by the appropriate techniques. It is likewise possible to use the zeolite in the form of pastilles, tablets, or in powder form if it is used in a fluidized bed.

The platinum can be deposited on the carrier by the methods described in the prior art. It is generally done by means of an aqueous solution, in particular by impregnation and exchange of ions. The impregnation can be effected with any platinum compound soluble in water such as hexachloroplatinic acid. Although this compound is satisfactory, it brings a certain acidity to the catalyst and it is preferable to use a Keller complex tetramine platinum chloride, or dinitro diaminoplatinum. Since dinitro diaminoplatinum is not very soluble in water, this impregnation can be effected hot. It is equally possible to use a platinum cationic complex, to make an ion exchange. In this case, the carrier is immersed in the solution containing the platinum, then it is withdrawn after a certain period of time, washed and dried. In fact, since the amounts of platinum to be deposited represent only a very small fraction of the cations of the zeolite and the zeolite has a strong affinity for platinum, the platinum remains totally fixed on the carrier. It is thus possible to deposit the Keller complex and different other cationic complexes of platinum and the dinitritódiaminoplatinum even though the latter is not an ionized compound. It is equally possible to effect the ion exchange in the presence of an excess of a salt of the cation of the zeolite, for instance, potassium chloride for the KL zeolite, so as more homogeneously to distribute the platinum in the structure of zeolite.

The amount of platinum to be introduced onto the carrier can range from about 0.1 to 1.5% by weight. In the bifunctional catalysts which have a base of platinum on chlorinated alumina, an amount of platinum above 0.3% has no additional influence on the dehydrocycling activity, for the acid function then limits the activity. To the contrary, the catalysts of the present invention have only a metallic function with a high dehydrocyclizing activity. The activity of the catalyst of the present invention increases monotonously with the amount of metal present in the catalyst. In practice, the activity is noticable at about 0.1% Pt. and increases beyond 1.5% Pt. However, at high platinum contents, the price of the catalyst becomes too high.

Rhenium must be deposited by using rhenium carbonyl $Re_2(CO)_{10}$. In fact, the method of aqueous impregnation of perrhenic acid results in catalysts of little activity and stability. A preferred method of the invention, therefore, comprises mixing the solid carrier with or without the platinum with powdered rhenium carbonyl, then heating at temperatures ranging from 50° to 200° C. This step can be carried out under a vacuum of from about 0.01 to 100 torrs to facilitate the sublimation.

Thus, the rhenium can be homogeneously distributed in the zeolite structure and after reduction, it will be better dispersed and can thus interact with the platinum.

Another technique comprises impregnating the zeolitic carrier with a solution of $Re_2(CO)_{10}$ in an appropriate solvent such as acetone.

The amount of rhenium present in the catalyst is comprised of from about 0.1 to 1.5%. This amount must in fact be adjusted to the platinum content of the catalyst. In fact, if there is too much rhenium in relation to platinum, the rhenium contributes to the hydrogenolysis reaction producing methane and ethane to the detriment of the production of aromatics and hydrogen. The hydrogenolysis is partially inhibited by the sulphur. It is in fact preferable to maintain the percent of rhenium at values not too elevated in relation to those of platinum. However, the rhenium content must not be too low in relation to that of platinum if it is desired to obtain the effect of catalytic stabilization.

The proportion of rhenium in relation to platinum must be adjusted according to the conditions under which the catalyst is to be used. A decrease in pressure increases aromatization and reduces hydrogenolysis and stability. Rhenium is responsible for most of the hydrogenolysis and for the high stability of the catalysts. At high pressures of use (15 to 35 bars, for instance), the amount of rhenium must be less than that of platinum because the pressure in itself is sufficient to stabilize the catalyst, and it is preferable to limit the hydrogenolysis. At low pressure operation, it can be advantageous to use a catalyst containing more rhenium than platinum because the catalyst is stabilized by a large amount of rhenium and high hydrogenolyzing activity is not a problem.

Rhenium has strong hydrogenolyzing properties. A Pt-Re on zeolite catalyst is very strongly hydrogenolyzing and the production of aromatics from aliphatics is low. Unlike the phenomena described in U.S. Pat. No. 3,415,737 for the alumina carrier, this hydrogenolysis does not diminish much in the course of time and it is accompanied by deactivation of the aromatizing function. It is not possible under these conditions to provide good selectivity of the monometallic catalyst by letting the hydrogenolyzing function of the catalyst deactivate. It is then indispensable to poison selectively the hydrogenolyzing function by sulphur. This operation is ordinarily carried out on bifunctional catalysts and there are cited in the prior art, sulphur contents on the order of 0.05% to 2% by weight.

Since sulphur in fact selectively poisons the metallic function of the catalyst, it is evident that the sulphur content must be in proportion to the metal content, and we express this content by the value $$x = \frac{S}{Pt + Re}$$

in atoms.

The sulphurization of the dehydrocyclization catalysts of the prior art is carried out with about $x=2$. In the present invention, such a value is prohibitive because the catalysts are then totally poisoned. The recommended value of x in the present invention is between about 0.1 and 0.6. At such low values, the catalysts of the prior art maintain a high hydrogenolyzing activity. For example, in a prior art bifunctional catalyst containing 0.3% Re and 0.3% Pt on chlorinated alumina, if $x=0.6$ (the gravimetric percent of sulphur is 0.05%) the catalyst is not selective in aromatization.

Sulphur may be impregnated into the carrier by aqueous means in a separate step or at the same time as the platinum. For an aqueous impregnation, oxyanions of sulphur such as sulphate, thiosulphate, sulphite, and the like ions can be used. At the time of reduction of the catalyst, the sulphur oxyanions are reduced at least partially to form $H_2S$ which selectively poisons the catalyst. Sulphide ions can also be used.

Another method comprises injecting a sulphurated compound into the catalyst in the presence of hydrogen, and then reducing the catalyst. It is thus possible to use sulphurated hydrogen, mercaptans, and disulphides such as dimethyl disulphide. All these methods are equivalent and produce good catalysts.

When elements have been deposited on the carrier, the catalyst is dried. It can then be calcined in air between 100° and 600° C., but the calcination is not indispensable. It is then placed in a reactor and reduced by hydrogen at a temperature between about 300° and 550° C.

The catalyst is used in processes of production of aromatics from petroleum fractions either in the production of motor fuels or in the production of petrochemical base stocks (benzene, toluene, xylene), charge and on the products desired. The operating pressure in fact can range between atmospheric pressure and 30 bars low pressures favor the yield of aromatics and accelerate coke formation on the catalyst. A pressure between 5 bars and 25 bars will be preferably used.

The operating temperature ranges between 420° and 600° C. High temperatures favor yields of aromatics. The temperature factor has an important influence on the yields. When operating at 14 bars with an n-hexane charge, the bifunctional catalysts of the prior art give an optimum of aromatics yield of 22% at temperatures on the order of 525° C. At higher temperatures, hydrocracking becomes prevalent and the yield of armoatics diminishes. On the other hand, using the catalysts of the present invention, there is obtained under these conditions, 30% of aromatics. If the temperature is raised to 550° C., it is possible to obtain up to 50% yield of aromatics from n-hexane at 14 bars.

It is necessary to include hydrogen in the charge contacting the catalyst to ensure catalyst stability. It is preferable to provide from 1 to about 10 moles of hydrogen per mole of hydrocarbon. The volume of charge which contacts the apparent volume of catalyst per hour will be from about 0.2 to 5 hours.

The catalysts of the invention can be used in reforming and aromatization processes. The hydrocarbon charges that can be used are the hydrocarbon charges usually introduced into the processes. The hydrocarbon charged must contain 1 ppm S or less, for the catalyst is sensitive to poisoning. For the precess to be economically interesting, the hydrocarbon charge must contain aliphatic or alicyclic hydrocarbons. The ideal charges are desulphurated fractions of distillation of petroleum, the initial distillation point of which is from about 50° to 120° C. and the final point from about 70° to 200° C.

A 50°-80° C. fraction contains hydrocarbons with 6 carbon atoms and essentially produces benzene. A 60°-100° C. fraction produces a mixture of benzene and toluene. Finally a 80°-180° C. fraction produces with an excellent yield, a fraction with a good octane index, but due to the properties of the catalysts, the fraction contains substantially more benzene and toluene than the fraction produced by classical processes and its final point is only slightly increased.

This invention will be better understood in light of the examples that follow.

In the examples, the hydrocarbon feed is a distillation fraction of 60°–80° C. interval, containing 91% of $C_6$ hydrocarbons of which 1% is benzene and 1.5% cyclohexane. The charge is desulphurated. The catalysts are reduced by hydrogen at 500° C., then tested in a reactor without hydrogen recycling under the following conditions: pressure 15 bars, molar ratio hydrogen to hydrocarbon 1:5, weight of charge injected per weight of catalyst and per hour 2.5 $h^{-1}$. The temperature is kept constant at 525° C. in the course of time and the evolution of the yields is followed for assessing the stability. Since the charge contains 3.5% benzene and $C_6$ naphthenes, it can be considered that the dehydrocyclizing activity is null when the yield in aromatics is less than or equal to 4%.

EXAMPLE 1

A monometallic catalyst with 0.6% Pt deposited by exchange of a Keller complex on a zeolite L under its potassium (KL) form is prepared by impregnation with a solution of Pt $(NH_3)_4Cl_2$ and KCl, washing, drying and calcination in air at 480° C.

After reduction by hydrogen, the following results are obtained:

| Operating time (hours) | Yield of $C_1$–$C_2$ Hydrocarbons (% by weight) | Yield of Aromatics (% by weight) |
| --- | --- | --- |
| 5 | 13.1 | 37.7 |
| 29 | 7.0 | 22.9 |
| 77 | 2.5 | 6.9 |

This example shows the excellent initial activity for dehydrocyclization, but the poor stability of the monometallic catalysts on zeolite L.

EXAMPLE 2

A commercial catalyst containing 0.3% platinum, 0.3% rhenium, 1.3% chlorine on alumina was placed in the reactor. After reduction by hydrogen, sulphuration by the dimethyl disulphide in the presence of hydrogen at 370° C. so as to inject 0.2% by weight of sulphur on the catalyst, that is $x=2$. The reaction is then effected under the above stated conditions.

The results are the following:

| Operating Time (hours) | Yield of $C_1$–$C_2$ hydrocarbons (% by wt.) | Yield of aromatics (% by wt.) |
| --- | --- | --- |
| 5 | 24.6 | 37.7 |
| 29 | 22.1 | 22.3 |
| 77 | 19.2 | 22.8 |

The commercial bifunctional catalyst is very stable but the yield in aromatics is not high.

EXAMPLE 3

Another sample of the commercial catalyst described in the preceding experiment is sulphurated at 0.06% by weight, where $x=0.6$, all the other parameters remaining the same.

There is obtained then:

| Operating time (hours) | Yield $C_1$–$C_2$ Hydrocarbons (% by wt.) | Yield of Aromatics (% by wt.) |
| --- | --- | --- |
| 5 | 72 | 10 |
| 29 | 65 | 15 |
| 77 | 61 | 14 |

This example clearly shows that the catalysts of the prior art do not tolerate only a small amount of sulphuration ($x=0.6$) since the hydrogenolysis to $C_1$–$C_2$ $C_2$ becomes very inportant, the aromatizing function is extremely reduced and never returns to the level of that of Example 2.

EXAMPLE 4

A catalyst having 0.6% Pt and 0.3% Re on the KL zeolite is prepared from the non-calcined catalyst of Example 1. This catalyst is impregnated by a solution of perrhenic acid, then dried and calcined in air at 480° C.

The results are the following:

| Operating Time (hours) | Yield $C_1$–$C_2$ Hydrocarbons (% by wt.) | Yield of Aromatics (% by wt.) |
| --- | --- | --- |
| 24 | 17 | 11 |
| 72 | 9 | 3.5 |

These results show that unlike the catalysts with the alumina carrier, the introduction of rhenium in the form of perrhenic acid is unfavorable to the catalyst: its activity is lower than that of the monometallic catalyst and the aromatization and hydrogenolysis activity is low and unstable. At 72 hours, the dehydrocyclizing activity becomes zero.

EXAMPLE 5

A catalyst with 0.6% Pt - 0.6% Re on KL zeolite was prepared as follows: the carrier was mixed with the necessary amount of $Re_2(CO)_{10}$, it was heated under a vacuum of 1 torr at 110° C. for 3 hours. After cooling, 60 g of catalyst was impregnated with 66 ml of KCl 0.1 N solution containing the necessary amount of $Pt(NH_3)_4Cl_2$. The catalyst was then washed and thereafter dried and calcined for 3 hours at 480° C.

| Operating Time (hours) | Yield of $C_1$–$C_2$ Hydrocarbons (% by wt.) | Yield of Aromatics (% by wt.) |
| --- | --- | --- |
| 5 | 76.7 | 6 |
| 28 | 70.4 | 5.6 |
| 52 | 64.3 | 5 |

Although not selective in aromatization, this catalyst becomes active because it is strongly hydrogenolyzing. This shows in relation to the preceding example that the use of the rhenium carbonyl instead of the perrhenic acid provides a catalyst with high activity. However, most of the activity is hydrogenolysis which is not a desirable reaction.

EXAMPLE 6

The catalyst of the preceding example is impregnated with an aqueous solution containing sodium sulphate so as to introduce 0.1 mole sulphur per Pt+Re($x=0.1$). It is tested after drying:

| Operating Time (hours) | Yield C$_1$-C$_2$ Hydrocarbons (% by wt.) | Yield of Aromatics (% by wt.) |
| --- | --- | --- |
| 5 | 56.7 | 10.7 |
| 29 | 36.6 | 14.6 |
| 77 | 22.5 | 13.5 |

The hydrogenolysis decreases while the aromatization is superior to that of the preceding example and is remains stable.

EXAMPLE 7

The catalyst of Example 5 is impregnated with an aqueous solution containing sodium sulphate so that $x=1$.

| Operating Time (hours) | Yield C$_1$-C$_2$ Hydrocarbons (% by wt.) | Yield of Aromatics (% by wt.) |
| --- | --- | --- |
| 5 | 12.6 | 5.3 |
| 24 | 8.5 | 4.3 |
| 52 | 6.1 | 4.6 |

It is seen that a sulphur atom introduced per metal atom poisons the catalyst. Both the hydrogenolysis and aromatization decrease remarkably in relation to the preceding example. The sulphur excess poisons both the aromatizing and hydrogenolyzing functions and the best value of x is between 0 and 1.

EXAMPLE 8

A catalyst identical with that of Example 6 is prepared, but it contains 0.6% Pt and 0.3% Re instead of 0.6% Pt and 0.6& Re. x is equal to 0.1.

| Operating Time (hours) | Yield C$_1$-C$_2$ Hydrocarbons (% by wt.) | Yield of Aromatics (% by wt.) |
| --- | --- | --- |
| 5 | 56.2 | 14.9 |
| 29 | 34.8 | 21.1 |
| 77 | 18.4 | 20.5 |

The smaller amount of rhenium in relation to the platinum reduces the hydrogenolysis but substantially increases the yield of aromatics.

EXAMPLE 9

A catalyst having 0.6% Pt - 0.3% Re on KL zeolite is prepared by impregnation by Pt (NH$_3$)$_2$(NO$_2$)$_2$ dissolved in a boiling solution of 0.1 N of KCl. After washing and drying, the catalyst is calcined at 400° C., then the rhenium carbonyl is introduced by the method described in Example 5. Finally, the catalyst is impregnated with a Na$_2$SO$_4$ solution so that $x=0.1$.

| Operating Time (hours) | Yield C$_1$-C$_2$ Hydrocarbons (% by wt.) | Yield of Aromatics (% by wt.) |
| --- | --- | --- |
| 5 | 48 | 20 |
| 29 | 28 | 23.2 |
| 77 | 18 | 22 |

EXAMPLE 10

The catalyst of the preceding example is not treated with Na$_2$SO$_4$ but it is treated in the reactor after reduction by hydrogen with an equivalent amount of sulphur ($x=0.1$) in the form of dimethyl disulphide at 370° C.

| Operating Time (hours) | Yield C$_1$-C$_2$ Hydrocarbons (% by wt.) | Yield of Aromatics (% by wt.) |
| --- | --- | --- |
| 25 | 40.1 | 25.1 |
| 73 | 32.0 | 21.0 |

The catalyst prepared by sulphuration with dimethyl disulphide is substantially equivalent to that obtained by sulfuration with Na$_2$SO$_4$.

EXAMPLES 11 TO 15

A series of catalysts with variable contents of platinum, rhenium and sulphur were prepared as follows:

Impregnation of the KL zeolite support by Pt (NH$_3$)$_2$(NO$_2$)$_2$ dissolved in a boiling solution of 0.1 N of KCl, washing and drying.

Deposition of rhenium carbonyl by sublimation on the zeolite at 2 torrs and 110° C.

Impregnation with a solution of Na$_2$SO$_4$ and drying. The following results are obtained after 77 hours of operation:

| Examples | %-Pt | % Re | x | Yield C$_1$-C$_2$ Hydrocarbons (% by wt.) | % Aromatics (% by wt.) |
| --- | --- | --- | --- | --- | --- |
| 11 | 1 | 0.67 | 0.22 | 18.9 | 28.2 |
| 12 | 1 | 0.67 | 0.47 | 16.5 | 27.0 |
| 13 | 0.6 | 0.55 | 0.6 | 8.3 | 10.3 |
| 14 | 1 | 0.32 | 0.35 | 6.2 | 10.9 |
| 15 | 0.6 | 0.55 | 0.35 | 19.0 | 22.6 |

EXAMPLE 16

A catalyst having the same metal and sulphur concentrations as the catalyst of Example 11 was prepared by impregnation with perrhenic acid instead of sublimation of rhenium carbonyl. There is obtained:

| Operating Time (Hours) | Yield C$_1$-C$_2$ Hydrocarbons (% by wt.) | Yield of Aromatics (% by wt.) |
| --- | --- | --- |
| 5 | 8.0 | 16.1 |
| 53 | 4.1 | 7.9 |

This example shows that the use of the perrhenic acid is damaging to the good catalytic properties of the Pt-Re-S- KL system.

EXAMPLE 17

A catalyst containing 0.87% Pt - 1% Re on KL zeolite with $x=0.1$ is prepared as described in Example 11 except that the step of sublimation of RE$_2$(CO)$_{10}$ is replaced by an impregnation of a solution of Re$_2$(CO)$_{10}$ in acetone.

The following results are obtained:

| Operating Time (hours) | Yield C$_1$-C$_2$ Hydrocarbons (% by wt.) | Yield of Aromatics (% by wt.) |
| --- | --- | --- |
| 3 | 46.5 | 16.8 |
| 24 | 30.5 | 17.2 |

-continued

| Operating Time (hours) | Yield C₁-C₂ Hydrocarbons (% by wt.) | Yield of Aromatics (% by wt.) |
|---|---|---|
| 72 | 25.1 | 16.5 |

Even though this catalyst contains a relatively large amount of rhenium and a small amount of sulphur, it has an interesting activity and excellent stability which shows that the catalysts of the invention can be prepared both by impregnation of rhenium carbonyl in acetone and by direct sublimation.

EXAMPLE 18

A catalyst having the same metal and sulphur concentrations as the catalyst of Example 11 was prepared using a carrier of faujasite NaX instead of the L zeolite.

| Operating Time (Hours) | Yield C₁-C₂ Hydrocarbons (% by wt.) | Yield of Aromatics (% by wt.) |
|---|---|---|
| 5 | 42 | 23 |
| 24 | 36 | 24.2 |
| 77 | 28.6 | 23.1 |

Although inferior to the catalyst having the L zeolite base, the catalyst shows interesting properties in aromatization and is stable.

EXAMPLE 19

A catalyst containing 0.87% Pt, 1% Re and x=0.1 was prepared by the method used for preparing the catalyst of Example 11. After reduction by hydrogen at 500° C., this catalyst was tested under the following conditions: pph 2.5 h$^{-1}$, H$_2$/HC 5, 500° C. instead of 525° C. and 8 bars instead of 15 bars.

The following results are obtained:

| Operating Time (hours) | Yield C₁-C₂ Hydrocarbons (% by wt.) | Yield of Aromatics (% by wt.) |
|---|---|---|
| 24 | 13.0 | 38.2 |
| 73 | 9.5 | 35.0 |

Although this catalyst contains more rhenium than platinum, it provides very good yields and selectivities for aromatics while maintaining a good stability. Since it is used at a lower pressure than in the preceding examples, the strong hydrogenolysis caused by the rhenium is inhibited by the low pressure while the yield in aromatics is favored and the high content of rhenium contributes to improving the stability of the catalyst.

We claim:

1. A process for preparing a bimetallic catalyst for the dehydrocyclization of paraffins comprising a carrier comprised of a zeolitic crystalline aluminosilicate exchanged with more than 90% of alkali metal cations and having a pore diamter larger than 6.5 Angstroms; 0.1 to 1.5% platinum; 0.1 to 1.5% rhenium obtained from rhenium carbonyl, the ratio of the rhenium/platinum varying with the pressure of use; a small amount of sulphur such that the ratio x of the number of sulphur atoms to platinum and rhenium atoms is from betweeon about 0.05 and 0.6, said process comprising the impregnating steps carried out in any desired order (a) charging the carrier with rhenium by sublimation of rhenium carbonyl;

(b) impregnating the carrier with an aqueous solution or water soluble complex of platinum;

(c) incorporating sulphur into the carrier by contacting with a sulphur containing compound;

(d) the impregnated carrier having received the charges of rhenium carbonyl, platinum complex, and sulphur compound being then dried, optionally calcined, and reduced by hydrogen at a temperature from about 300° C. to 500° C. prior to use.

2. A dehydrocyclization catalyst according to claim 1, wherein for use at a pressure of about 15 bars to 35 bars the proportion of rhenium is less than that of platinum.

3. A dehydrocyclization catalyst according to claim 1, wherein for use at low pressure, the content of rhenium is more than that of platinum whereby its stability is maintained.

4. A catalyst according to claim 1, wherein the carrier is selected from the group consisting of faujasite X, faujasite Y, zeolite L, zeolite omega and zeolite ZSM 4.

5. A catalyst according to claim 4, wherein the carrier is an exchange zeolite L containing at least one of the alkali metals selected from the group consisting of sodium, potassium, rubidium and cesium.

6. A catalyst according to claim 1 wherein the carrier is in the shape of small balls, tablets or pastilles.

7. A catalyst of claim 1 wherein the atomic ratio of platinum to rhenium is from about 3:1 to about 0.87:1.

8. The process of claim 1 wherein the aqueous solution or water soluble complex of platinum is selected from the group consisting of solutions of hexachloroplatinic acid tetramine platinum chloride and dinitrodiaminoplatinum.

9. The process of claim 1 wherein the carrier is impregnated by exchange of ions with cationic complex of platinum.

10. The process of claim 9 wherein the cationic complex of platinum is in an aqueous solution of an excess of a salt of the zeolite cation.

11. The process of claim 1, wherein the carrier is charged with rhenium by sublimation of rhenium carbonyl at a pressure of from about 0.01 to 100 tors.

12. The process of claim 1 wherein the sulphur is incorporated into the carrier by pretreatment of the carrier charged with rhenium and platinum in the dehydrocyclization reactor by contact with a sulphur containing compound selected from the group consisting of hydrogen sulphide, dimethyl disulphide and carbon disulphide.

13. A process for making a bimetallic catalyst for the dehydrocyclization of paraffins, comprising a carrier comprised of a zeolitic crystalline aluminosilicate exchanged with more than 90% of alkali metal cations and having a pore diameter larger than 6.5 Angstroms; 0.1 to 1.5% platinum; 0.1 to 1.5% rhenium obtained from rhenium carbonyl, the ratio of the rhenium/platinum varying with the pressure of use; a small amount of sulphur such that the ratio x of the number of sulphur atoms to platinum and rhenium atoms is from between about 0.05 and 0.6, said process comprising the impregnating steps carried out in any order desired:

(a) charging the carrier with rhenium by impregnation with a solution of rhenium carbonyl in acetone;

(b) impregnating the carrier with an aqueous solution or water soluble complex of platinum;

(c) impregnating sulphur by impregnation of the carrier with a solution of a sulphur containing compound; and (d) after the impregnation steps, drying, heat treating and reducing the impregnated carrier with hydrogen at a temperature between about 300° C. and 550° C. prior to use.

14. A bimetallic catalyst prepared by the method of claim 1 or 13.

15. A process of claim 13 for making the catalyst of claim 14 wherein the sulphur is incorporated onto the carrier by pretreatment of the carrier charged with rhenium and platinum in the dehydrocyclization reactor by contact with a sulphur containing compound selected from the group consisting of hydrogen sulphide, dimethyl disulphide, and carbon disulphide.

16. The process of claim 13 wherein the solution of a sulphur containing compound is selected from the group consisting of sulphates, thiosulphates and sulphites.

17. The process of claim 13, wherein the carrier is impregnated with a composition selected from the group consisting of hexachloroplatinic acid, tetramine platinum chloride, dinitrodiamino platinum and by exchange of ions with a cationic complex of the platinum.

18. The method of claim 17 wherein the cationic complex of platinum is in solution of an excess of a salt of the zeolite cation.

19. A bimetallic catalyst prepared by the method of claim 14.

20. A dehydrocyclization catalyst according to claim 19, wherein for use at a pressure of about 15 bars to 35 bars the proportion of rhenium is less than that of platinum.

21. A dehydrocyclization catalyst according to claim 19, wherein for use at low pressure, the content of rhenium is more than that of platinum whereby its stability is maintained.

22. A catalyst according to claim 19, wherein the carrier is selected from the group consisting of faujasite X, faujasite Y, zeolite L, zeolite omega and zeolite ZSM 4.

23. A catalyst according to claim 22, wherein the carrier is an exchange zeolite L containing at least one of the alkali metals selected from the group consisting of sodium, potassium, rubidium and cesium.

24. A catalyst according to claim 19, wherein the carrier is in the shape of small balls, tablets or pastilles.

25. A catalyst of claim 19 wherein the atomic ratio of platinum to rhenium is from about 3:1 to about 0.87:1.

26. The process of claim 8, wherein the carrier is charged with rhenium by sublimation of rhenium carbonyl at a pressure of from about 0.01 to 100 tors.

27. The process of claim 9, wherein the carrier is charged with rhenium by sublimation of rhenium carbonyl at a pressure of from about 0.01 to 100 tors.

28. The process of claim 10, wherein the carrier is charged with rhenium by sublimation of rhenium carbonyl at a pressure of from about 0.01 to 100 tors.

29. The process of claim 15, wherein the carrier is impregnated with a composition selected from the group consisting of hexachloroplactinic acid, tetramine platinum chloride, dinitrodiamino platinum and by exchange of ions with a cationic complex of the platinum.

30. The method of claim 29 wherein the cationic complex of platinum is in solution of an excess of a salt of the zeolite cation.

31. The process of claim 16, wherein the carrier is impregnated with a composition selected from the group consisting of hexachloroplatinic acid, tetramine platinum chloride, dinitrodiamino platinum and by exchange of ions with a cationic complex of the platinum.

32. The method of claim 31 wherein the cationic complex of platinum is in solution of an excess of a salt of the zeolite cation.

* * * * *